United States Patent
Xu

(10) Patent No.: US 9,089,408 B2
(45) Date of Patent: Jul. 28, 2015

(54) BIODEGRADABLE METALLIC MEDICAL IMPLANTS, METHOD FOR PREPARING AND USE THEREOF

(71) Applicant: Zhiyue Xu, Cypress, TX (US)

(72) Inventor: Zhiyue Xu, Cypress, TX (US)

(73) Assignee: Baker Hughes Incorporated, Houston, TX (US)

( * ) Notice: Subject to any disclaimer, the term of this patent is extended or adjusted under 35 U.S.C. 154(b) by 131 days.

(21) Appl. No.: 13/764,816

(22) Filed: Feb. 12, 2013

(65) Prior Publication Data

US 2014/0228972 A1    Aug. 14, 2014

(51) Int. Cl.

| | |
|---|---|
| *A61F 2/02* | (2006.01) |
| *A61F 2/08* | (2006.01) |
| *A61F 2/28* | (2006.01) |
| *A61L 27/58* | (2006.01) |
| *A61L 27/42* | (2006.01) |
| *A61L 31/12* | (2006.01) |
| *A61L 31/14* | (2006.01) |
| *A61L 17/06* | (2006.01) |
| *A61B 17/68* | (2006.01) |
| *A61B 17/00* | (2006.01) |

(52) U.S. Cl.
CPC . *A61F 2/02* (2013.01); *A61B 17/68* (2013.01); *A61L 17/06* (2013.01); *A61L 27/427* (2013.01); *A61L 27/58* (2013.01); *A61L 31/124* (2013.01); *A61L 31/148* (2013.01); *A61B 2017/00004* (2013.01); *A61F 2210/0004* (2013.01); *A61L 2400/12* (2013.01)

(58) Field of Classification Search
CPC ..... A61F 2/02; A61F 2/28; A61F 2002/2835; A61F 2002/2839; A61F 2310/00011; A61F 2310/00395; A61B 17/68; A61L 17/06; A61L 27/58; A61L 31/148; A61L 2400/12
USPC ................. 623/23.72, 23.75, 23.76
See application file for complete search history.

(56) References Cited

U.S. PATENT DOCUMENTS

2007/0233112 A1*  10/2007  Orbay et al. ............. 606/69
2008/0175885 A1    7/2008  Asgari
(Continued)

FOREIGN PATENT DOCUMENTS

EP           2000551 A1   12/2008

OTHER PUBLICATIONS

Tanja Kraus et al., "Magnesium alloys for temporary implants in osteosynthesis: In vivo studies of their degradation and interaction with bone," 2011 Acta Materialia Inc. Published by Elsevier Ltd. All rights reserved, Acta Biomaterialia 8 (2012), p. 1230-1238.
(Continued)

*Primary Examiner* — Randy Shay
*Assistant Examiner* — Dinah Baria
(74) *Attorney, Agent, or Firm* — Cantor Colburn LLP

(57) ABSTRACT

A medical implant includes a metal composite that contains a cellular nanomatrix having a metallic nanomatrix material and a metal matrix disposed in the cellular nanomatrix, the medical implant being configured to disintegrate in response to contact with a fluid. A method for repairing tissue includes disposing an implant in a patient, the implant including a metal composite which contains: a cellular nanomatrix having a metallic nanomatrix material; and a metal matrix disposed in the cellular nanomatrix; contacting tissue of the patient with the implant, the tissue being in need of repair; and non-operatively removing the implant to repair the tissue.

15 Claims, 10 Drawing Sheets

(56) References Cited

U.S. PATENT DOCUMENTS

2008/0249638 A1 10/2008 Asgari
2010/0222873 A1 9/2010 Atanasoska et al.
2011/0046721 A1 2/2011 Arps
2012/0103135 A1 5/2012 Xu et al.

OTHER PUBLICATIONS

Zhang et al., "In vivo evaluation of biodegradable magnesium alloy bone implant in the first 6 months implantation," Journal of Biomedical Materials Research Part A, 2008 Wiley Periodicals, Inc., p. 882-893.

Song et al., "A Possible BiodegradableMagnesium ImplantMaterial," Copyright 2007 Wiley-VCH Verlag GmbH & Co. KGaA,Weinheim, Advanced Engineering Materials 2007, 9, No. 4.

International Search Report and Written Opinion, Date of Mailing Apr. 1, 2014, International Application No. PCT/US2014/010861, Korean Intellectual Property Office, International Search Report 6 pages; Written Opinion 6 pages.

* cited by examiner

US 9,089,408 B2

BIODEGRADABLE METALLIC MEDICAL IMPLANTS, METHOD FOR PREPARING AND USE THEREOF

BACKGROUND

Implantation of medical implants represents a significant proportion of surgical procedures. Besides cosmetic and reconstructive surgery, it is common to have a subsequent surgery to remove an implant after the implant has either successfully or unsuccessfully performed its task. For example, orthopedic implants join broken bone or fuse separated bones. These implants also align and hold bones in relative positions. Additionally, some implants are used with spine, skull, and other skeletal parts such as on the flat surface of a bone (e.g., a scapula or pelvis) or on a tubular bone (e.g., humerus, radius, femur, or tibia).

Some implants impede mass transfer to or from a site below or surrounding the implant. Consequently, the implant may slow or disrupt regeneration and osteosynthesis of bone or tissue that is to be healed. Additionally, some implants can incur hardware breakage, loosening, insufficient flexibility, inability to gain adequate fixation, unnecessary additional weight, and other problems related to the implant or recovery of the patient. For example, an implant can impart distraction pseudoarthrosis, where the implant disallows a portion of tissue, e.g., bone, to come together over time, resulting in failure of solid bone healing. Relatedly, some implants that remain intact without mass loss during tissue regeneration provide slow patient recovery due to the implant artificially blocking damaged tissue from beneficial secretions, oxygenation, or tissue contact. Such issues can cause other problems, be associated with surgical failure, or require further surgical procedures to repair damage, remove failed hardware, or reattempt stabilization of anatomy.

Advances in materials and methods for implantation and for enhancement of patient recovery or amelioration of negative biological effects are well received by the industry.

BRIEF DESCRIPTION

The above and other deficiencies are overcome by, in an embodiment, an implant comprising: a metal composite which comprises: a cellular nanomatrix comprising a metallic nanomatrix material; and a metal matrix disposed in the cellular nanomatrix, the medical implant being configured to disintegrate in response to contact with a fluid.

In another embodiment, a method for repairing tissue, the method comprises: disposing an implant in a patient, the implant comprising a metal composite which comprises: a cellular nanomatrix comprising a metallic nanomatrix material; and a metal matrix disposed in the cellular nanomatrix; contacting tissue of the patient with the implant, the tissue being in need of repair; and non-operatively removing the implant to repair the tissue.

BRIEF DESCRIPTION OF THE DRAWINGS

The following descriptions should not be considered limiting in any way. With reference to the accompanying drawings, like elements are numbered alike.

DETAILED DESCRIPTION

A detailed description of one or more embodiments is presented herein by way of exemplification and not limitation.

It has been found that metal containing controlled electrolytic metallic (CEM) can beneficially be used for medical implants. Such an implant is biocompatible, lightweight, and nonmagnetic and has a modulus of elasticity closer to bone or other tissue than currently used implantable materials, e.g., a polymer. The implant herein biodegrades by disintegration in vivo without an extra surgery to remove it from a patient. Moreover, the material of the implant has a composition and microstructure that can be configured at the micro or nanoscale to control the material strength, ductility, or disintegration rate.

Furthermore, the implant herein can be made by powder metallurgy by consolidating metal powders coated with a biocompatible metal or ceramic. The composition and microstructure of the implant thus is configured at the micro or nanoscale for a select dissolution rate while establishing a uniformity of the exterior and interior structure. Hence, as the implant disintegrates, it retains its geometrical shape and strength in the remaining portion throughout the disintegration period.

Moreover, the high strength, high ductility yet fully disintegrable and biocompatible medical implant can be made from materials that selectively and controllably disintegrate in response to contact with certain fluids, e.g., biological or biocompatible fluids. Such a disintegrable implant includes components that are selectively corrodible and have selectively tailorable disintegration rates and selectively tailorable material properties. Additionally, the disintegrable implant can have components that have varying compression, tensile strength, or disintegration rate. As used herein, "disintegrable" refers to a material, component, or article that is consumable, corrodible, degradable, dissolvable, weakenable, or otherwise removable. It is to be understood that use herein of the term "disintegrate," or any of its forms (e.g., "disintegration"), incorporates the stated meaning.

According to an embodiment, an implant includes a metal composite. The metal composites include a cellular nanomatrix comprising a metallic nanomatrix material and a metal matrix disposed in the cellular nanomatrix. The implant is configured to disintegrate in response to contact with a fluid.

Figure 1:
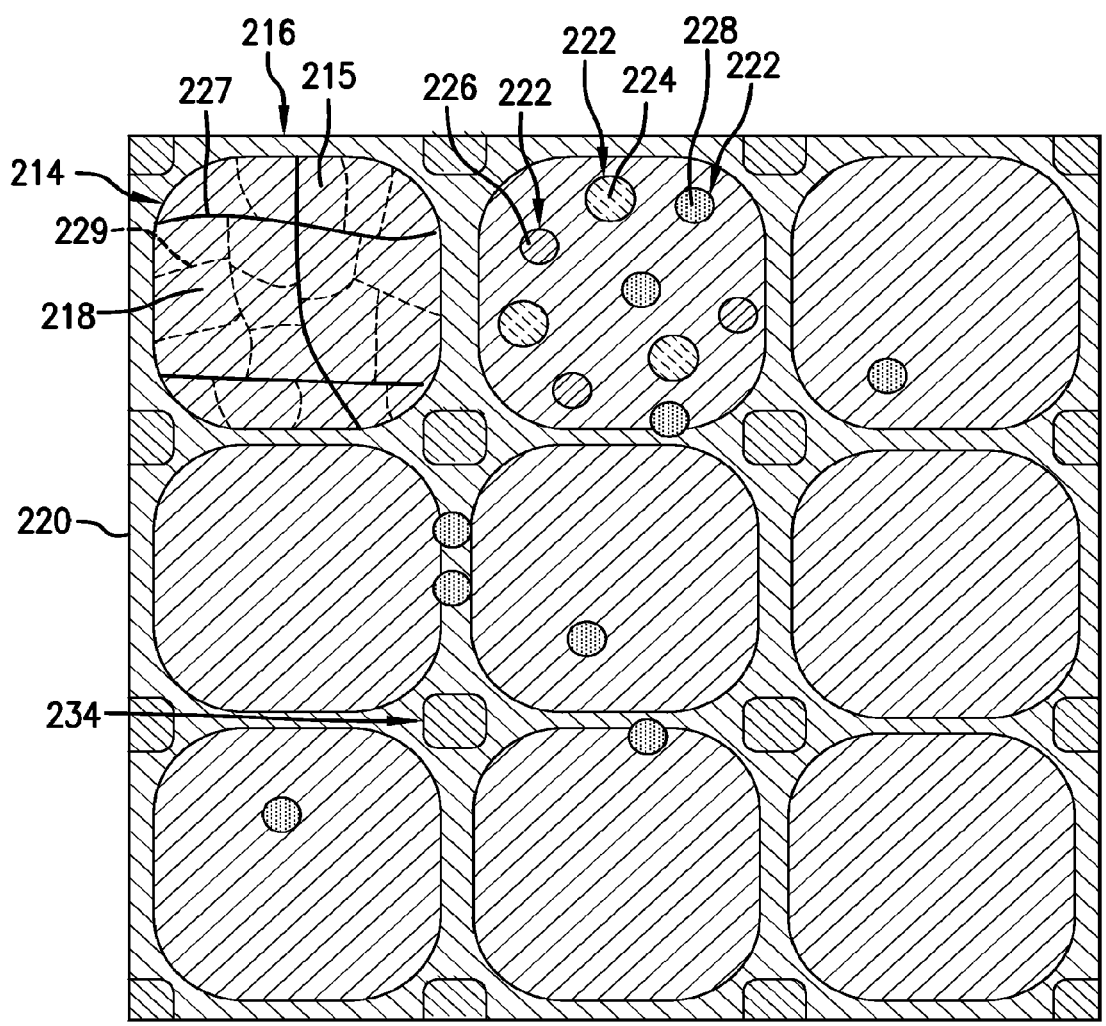
FIG. 1 depicts a cross sectional view of a disintegrable metal composite.

The metal composite is, for example, a powder compact as shown in FIG. 1. The metal composite 200 includes a cellular nanomatrix 216 comprising a nanomatrix material 220 and a metal matrix 214 (e.g., a plurality of dispersed particles) comprising a particle core material 218 dispersed in the cellular nanomatrix 216. The particle core material 218 comprises a nanostructured material. Such a metal composite having the cellular nanomatrix with metal matrix disposed therein is referred to as controlled electrolytic metallic.

Figure 3:
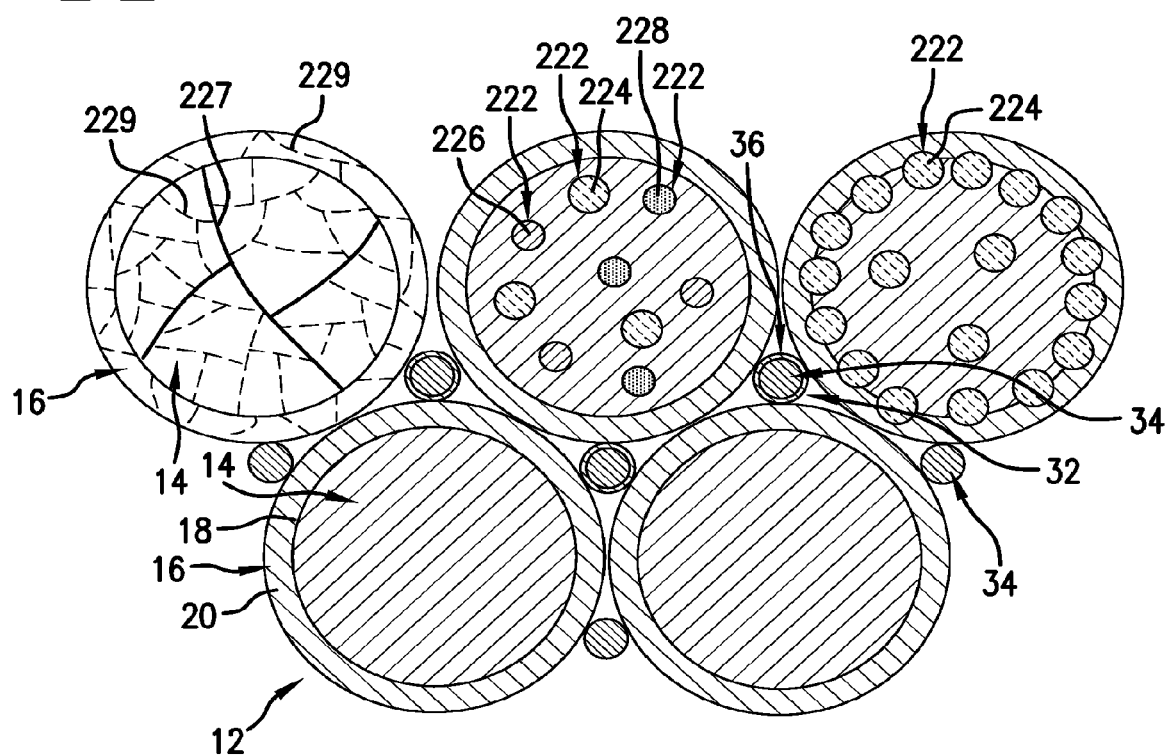
FIG. 3 depicts a cross sectional view of a composition used to make the disintegrable metal composite shown in FIG. 1.

With reference to FIGS. 1 and 3, metal matrix 214 can include any suitable metallic particle core material 218 that includes nanostructure as described herein. In an exemplary embodiment, the metal matrix 214 is formed from particle cores 14 (FIG. 3) and can include an element such as magnesium, aluminum, calcium, iron, manganese, zinc, copper, or a combination thereof, as the nanostructured particle core material 218. In one embodiment, the metal matrix 214 and particle core material 218 is magnesium. In another exemplary embodiment, the metal matrix 214 and particle core material 218 includes various Mg alloys as the nanostructured particle core material 218, including various precipitation hardenable Mg alloys. In some embodiments, the particle core material 218 includes magnesium and a biocompatible alloying element (e.g., aluminum, zinc, calcium, zinc, and the like) where the alloying element is present in an amount from 0.01 weight percent (wt %) to 15 wt %, specifically 0.05 wt % to 10 wt %, more specifically 0.05 wt % to 5 wt %, and yet more specifically 0.1 wt % to 2 wt %, based on the weight of the metal matrix, the balance of the weight being magnesium.

In an embodiment, the metal matrix includes magnesium. The metal matrix can further include elements such as aluminum, copper, silicon, manganese, nickel, zinc, iron, calcium, or a combination thereof. In one embodiment, the metal matrix is an alloy. The magnesium alloy can include the following magnesium series of alloys AZ, AM, HK, HM, HZ, M, QE, QH, WE, ZC, ZE, ZK, or a combination thereof In an additional embodiment, precipitation hardenable Mg alloys are particularly useful because they can strengthen the metal matrix 214 through both nanostructuring and precipitation hardening through the incorporation of particle precipitates as described herein.

The metal matrix 214 and particle core material 218 also can include a nanostructured material 215. In an exemplary embodiment, the nanostructured material 215 is a material having a grain size (e.g., a subgrain or crystallite size) that is less than 200 nanometers (nm), specifically 10 nm to 200 nm, and more specifically an average grain size less than 100 nm. The nanostructure of the metal matrix 214 can include high angle boundaries 227, which usually are used to define the grain size, or low angle boundaries 229 that can occur as substructure within a particular grain, which are sometimes used to define a crystallite size, or a combination thereof. It should be appreciated that the nanocellular matrix 216 and grain structure (nanostructured material 215 including grain boundaries 227 and 229) of the metal matrix 214 are distinct features of the metal composite 200. Particularly, nanocellular matrix 216 is not part of a crystalline or amorphous portion of the metal matrix 214.

In an embodiment, the implant can also include an optional disintegration agent. The disintegration agent is disposed in the metal matrix. In another embodiment, the disintegration agent is disposed external to the metal matrix. In yet another embodiment, the disintegration agent is disposed in the metal matrix as well as external to the metal matrix. The metal composite also includes the cellular nanomatrix that comprises a metallic nanomatrix material. The disintegration agent can be disposed in the cellular nanomatrix among the metallic nanomatrix material. An exemplary metal composite and method used to make the metal composite are disclosed in U.S. patent application Ser. Nos. 12/633,682, 12/633,688, 13/220,832, 13/220,822, and 13/358,307, the disclosure of each patent application is incorporated herein by reference in its entirety.

The disintegration agent can be included in the metal composite 200 to control the disintegration rate of the metal composite 200. The disintegration agent can be disposed in the metal matrix 214, the cellular nanomatrix 216, or a combination thereof. According to an embodiment, the disintegration agent includes a metal, fatty acid, ceramic particle, or a combination thereof, the disintegration agent being disposed among the controlled electrolytic material to change the disintegration rate of the controlled electrolytic metallics. In one embodiment, the disintegration agent is disposed in the cellular nanomatrix external to the metal matrix. In an embodiment, the disintegration agent increases the disintegration rate of the metal composite 200. In another embodiment, the disintegration agent decreases the disintegration rate of the metal composite 200. The disintegration agent can be a metal including cobalt, copper, iron, nickel, zinc, or a combination thereof. In a further embodiment, the disintegration agent is the fatty acid, e.g., fatty acids having 6 to 40 carbon atoms. Exemplary fatty acids include oleic acid, stearic acid, lauric acid, hyroxystearic acid, behenic acid, arachidonic acid, linoleic acid, linolenic acid, recinoleic acid, palmitic acid, montanic acid, or a combination thereof. The disintegration agent can be present in an amount effective to cause disintegration of the metal composite 200 at a desired disintegration rate, specifically about 0.25 wt % to 15 wt %, specifically 0.25 wt % to 10 wt %, specifically 0.25 wt % to 1 wt %, based on the weight of the metal composite.

In an exemplary embodiment, the cellular nanomatrix 216 includes aluminum, calcium, molybdenum, cobalt, copper, iron, magnesium, nickel, silicon, zinc, an intermetallic compound thereof, or a combination thereof. The metal matrix can be present in an amount from 50 wt % to 95 wt %, specifically 60 wt % to 95 wt %, and more specifically 70 wt % to 95 wt %, based on the weight of the implant. Further, the amount of the metal nanomatrix material is 10 wt % to 50 wt %, specifically 20 wt % to 50 wt %, and more specifically 30 wt % to 50 wt %, based on the weight of the implant.

In another embodiment, the metal composite includes a second particle. As illustrated generally in FIGS. 1 and 3, the metal composite 200 can be formed using a coated metallic powder 10 and an additional or second powder 30, i.e., both powders 10 and 30 can have substantially the same particulate structure without having identical chemical compounds. The use of an additional powder 30 provides a metal composite 200 that also includes a plurality of dispersed second particles 234, as described herein, that are dispersed within the cellular nanomatrix 216 and are also dispersed with respect to the metal matrix 214. Thus, the dispersed second particles 234 are derived from second powder particles 32 disposed in the powder 10, 30. In an exemplary embodiment, the dispersed second particles 234 include Ca, Mo, Mg, Ni, Fe, Cu, Co, Al, Zn, Mn, Si, intermetallic compound thereof, or a combination thereof Referring again to FIG. 1, the metal matrix 214 and particle core material 218 also can include an additive particle 222. The additive particle 222 provides a dispersion strengthening mechanism to the metal matrix 214 and provides an obstacle to, or serves to restrict, the movement of dislocations within individual particles of the metal matrix 214. Additionally, the additive particle 222 can be disposed in the cellular nanomatrix 216 to strengthen the metal composite 200. The additive particle 222 can have any suitable size and, in an exemplary embodiment, can have an average particle size from 10 nm to 1 micrometer (μm), and specifically 50 nm to 200 nm. Here, size refers to the largest linear dimension of the additive particle. The additive particle 222 can include any suitable form of particle, including an embedded particle 224, a precipitate particle 226, or a dispersoid particle 228. Embedded particle 224 can include any suitable embedded particle, including various hard particles. The embedded particle can include various metal, carbon, metal oxide, metal nitride, metal carbide, intermetallic compound, cermet particle, or a combination thereof. In an exemplary embodiment, hard particles can include Ca, Mo, Mg, Ni, Fe, Cu, Co, Al, Zn, Mn, Si, an intermetallic compound thereof, or a combination thereof. The additive particle can be present in an amount from 0.5 wt % to 25 wt %, specifically 0.5 wt % to 20 wt %, and more specifically 0.5 wt % to 10 wt %, based on the weight of the metal composite.

In metal composite 200, the metal matrix 214 dispersed throughout the cellular nanomatrix 216 can have an equiaxed structure in a substantially continuous cellular nanomatrix 216 or can be substantially elongated along an axis so that individual particles of the metal matrix 214 are oblately or prolately shaped, for example. In the case where the metal matrix 214 has substantially elongated particles, the metal matrix 214 and the cellular nanomatrix 216 may be continuous or discontinuous. The size of the particles that make up the metal matrix 214 can be from 50 nm to 800 μm, specifically 500 nm to 600 μm, and more specifically 1 μm to 500 μm. The particle size can be monodisperse or polydisperse, and the particle size distribution can be unimodal or bimodal. Size here refers to the largest linear dimension of a particle.

Figure 2:
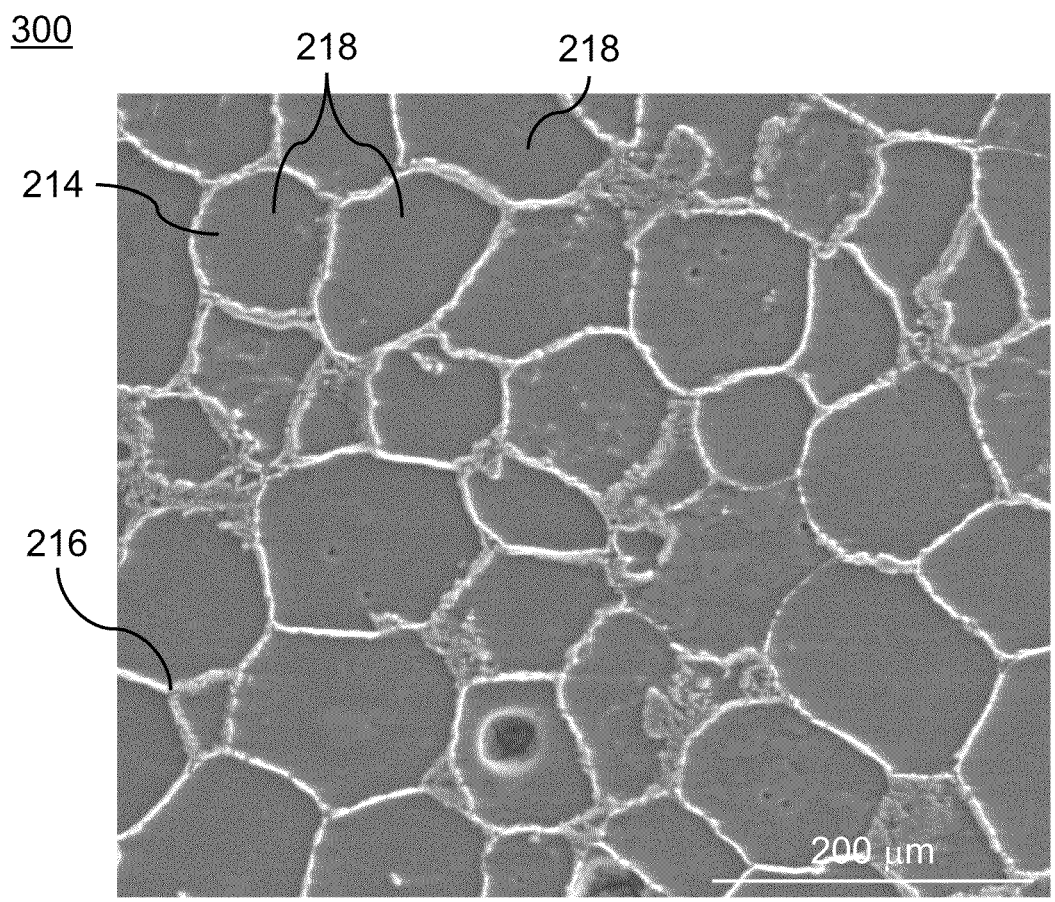
FIG. 2 is a photomicrograph of an exemplary embodiment of a disintegrable metal composite as disclosed herein.

Referring to FIG. 2 a photomicrograph of an exemplary embodiment of a metal composite is shown. The metal composite 300 has a metal matrix 214 that includes particles having a particle core material 218. Additionally, each particle of the metal matrix 214 is disposed in a cellular nanomatrix 216. Here, the cellular nanomatrix 216 is shown as a network that substantially surrounds the component particles of the metal matrix 214.

According to an embodiment, the metal composite is formed from a combination of, for example, powder constituents. As illustrated in FIG. 3, a powder 10 includes powder particles 12 that have a particle core 14 with a core material 18 and metallic coating layer 16 with coating material 20. In an embodiment, the powder particle 12 can include a plurality of coating layers 16, wherein each of the plurality of coating layers 16 can be the same or different composition. While it is contemplated that there is no upper limit to the number of coating layers 16, the number of coating layers 16 can be from 1 to 50, specifically 1 to 10, and more specifically 1 to 3. These powder constituents can be selected and configured for compaction and sintering to provide the metal composite 200 that is lightweight (i.e., having a relatively low density), high-strength, and selectably and controllably removable, e.g., by disintegration, from an implant in response to, e.g., contact with a fluid, including being selectably and controllably disintegrable (e.g., by having a selectively tailorable disintegration rate curve) in an appropriate fluid or biological environment (e.g., soft tissue, hard tissue, etc.).

The nanostructure can be formed in the particle core 14 that is used to form metal matrix 214 by any suitable method, including a deformation-induced nanostructure such as can be provided by ball milling a powder to provide particle cores 14, and more particularly by cryomilling (e.g., ball milling in ball milling media at a cryogenic temperature or in a cryogenic fluid, such as liquid nitrogen) a powder to provide the particle cores 14 used to form the metal matrix 214. The particle cores 14 may be formed as a nanostructured material 215 by any suitable method, such as, for example, by milling or cryomilling of prealloyed powder particles of the materials described herein. The particle cores 14 may also be formed by mechanical alloying of pure metal powders of the desired amounts of the various alloy constituents. Mechanical alloying involves ball milling, including cryomilling, of these powder constituents to mechanically enfold and intermix the constituents and form particle cores 14. In addition to the creation of nanostructure as described above, ball milling, including cryomilling, can contribute to solid solution strengthening of the particle core 14 and core material 18, which in turn can contribute to solid solution strengthening of the metal matrix 214 and particle core material 218. The solid solution strengthening can result from the ability to mechanically intermix a higher concentration of interstitial or substitutional solute atoms in the solid solution than is possible in accordance with the particular alloy constituent phase equilibria, thereby providing an obstacle to, or serving to restrict, the movement of dislocations within the particle, which in turn provides a strengthening mechanism in the particle core 14 and the metal matrix 214. The particle core 14 can also be formed with a nanostructure (grain boundaries 227, 229) by methods including inert gas condensation, chemical vapor condensation, pulse electron deposition, plasma synthesis, crystallization of amorphous solids, electrodeposition, and severe plastic deformation, for example. The nanostructure also can include a high dislocation density, such as, for example, a dislocation density from $10^{17}$ m$^{-2}$ to $10^{18}$ m$^{-2}$, which can be two to three orders of magnitude higher than similar alloy materials deformed by traditional methods, such as cold rolling. Thus, the particle core 14 can be formed and surrounded by metallic coating layer 16 in a powder process that can include cyromilling, ball milling, and the like. Further, non-mechanical processes such as chemical vapor deposition can be used to deposit coating layer 16 on particle core 14. Here, it should be appreciated that individual particle cores 14 will be coated independently from one another and will separately receive the coating layer 16.

The substantially-continuous cellular nanomatrix 216 (see FIG. 2) and nanomatrix material 220 formed from metallic coating layers 16 by the compaction and sintering of the plurality of metallic coating layers 16 with the plurality of powder particles 12, such as by cold isostatic pressing (CIP), hot isostatic pressing (HIP), dynamic forging, die forging, extrusion, injection molding, and the like. The chemical composition of nanomatrix material 220 may be different than that of coating material 20 due to diffusion effects associated with the sintering. The metal composite 200 also includes a plurality of particles that make up the metal matrix 214 that comprises the particle core material 218. The metal matrix 214 and particle core material 218 correspond to and are formed from the plurality of particle cores 14 and core material 18 of the plurality of powder particles 12 as the metallic coating layers 16 are sintered together to form the cellular nanomatrix 216. The chemical composition of particle core material 218 may also be different than that of core material 18 due to diffusion effects associated with sintering.

As used herein, the term cellular nanomatrix 216 does not connote the major constituent of the powder compact, but rather refers to the minority constituent or constituents, whether by weight or by volume. This is distinguished from most matrix composite materials where the matrix comprises the majority constituent by weight or volume. The use of the term substantially continuous, cellular nanomatrix is intended to describe the extensive, regular, continuous and interconnected nature of the distribution of nanomatrix material 220 within the metal composite 200. As used herein, "substantially continuous" describes the extension of the nanomatrix material 220 throughout the metal composite 200 such that it extends between and envelopes substantially all of the metal matrix 214. Substantially continuous is used to indicate that complete continuity and regular order of the cellular nanomatrix 220 around individual particles of the metal matrix 214 are not required. For example, defects in the coating layer 16 over particle core 14 on some powder particles 12 may cause bridging of the particle cores 14 during sintering of the metal composite 200, thereby causing localized discontinuities to result within the cellular nanomatrix 216, even though in the other portions of the powder compact the cellular nanomatrix 216 is substantially continuous and exhibits the structure described herein. In contrast, in the case of substantially elongated particles of the metal matrix 214 (i.e., non-equiaxed shapes), such as those formed by extrusion, "substantially discontinuous" is used to indicate that incomplete continuity and disruption (e.g., cracking or separation) of the nanomatrix around each particle of the metal matrix 214, such as may occur in a predetermined extrusion direction. As used herein, "cellular" is used to indicate that the nanomatrix defines a network of generally repeating, interconnected, compartments or cells of nanomatrix material 220 that encompass and also interconnect the metal matrix 214. As used herein, "nanomatrix" is used to describe the size or scale of the matrix, particularly the thickness of the matrix between adjacent particles of the metal matrix 214. The metallic coating layers that are sintered together to form the nanomatrix are themselves nanoscale thickness coating layers. Since the cellular nanomatrix 216 at most locations, other than the intersection of more than two particles of the metal matrix 214, generally comprises the interdiffusion and bonding of two coating layers 16 from adjacent powder particles 12 having nanoscale thicknesses, the cellular nanomatrix 216 formed also has a nanoscale thickness (e.g., approximately two times the coating layer thickness as described herein, and in some embodiments less) and is thus described as a nanomatrix. Further, the use of the term metal matrix 214 does not connote the minor constituent of metal composite 200, but rather refers to the majority constituent or constituents, whether by weight or by volume. The use of the term metal matrix is intended to convey the discontinuous and discrete distribution of particle core material 218 within metal composite 200. The distribution of individual particle core material 218 may or may not form a repeated pattern in the metal composite 200.

Embedded particle 224 can be embedded by any suitable method, including, for example, by ball milling or cryomilling hard particles together with the particle core material 18. A precipitate particle 226 can include any particle that can be precipitated within the metal matrix 214, including precipitate particles 226 consistent with the phase equilibria of constituents of the materials, particularly metal alloys, of interest and their relative amounts (e.g., a precipitation hardenable alloy), and including those that can be precipitated due to non-equilibrium conditions, such as may occur when an alloy constituent that has been forced into a solid solution of the alloy in an amount above its phase equilibrium limit, as is known to occur during mechanical alloying, is heated sufficiently to activate diffusion mechanisms that enable precipitation. Dispersoid particles 228 can include nanoscale particles or clusters of elements resulting from the manufacture of the particle cores 14, such as those associated with ball milling, including constituents of the milling media (e.g., balls) or the milling fluid (e.g., liquid nitrogen) or the surfaces of the particle cores 14 themselves (e.g., metallic oxides or nitrides). Dispersoid particles 228 can include an element such as, for example, Ca, Si, Mo, Fe, Ni, Cr, Mn, N, O, C, H, and the like. The additive particles 222 can be disposed anywhere in conjunction with particle cores 14 and the metal matrix 214. In an exemplary embodiment, additive particles 222 can be disposed within or on the surface of metal matrix 214 as illustrated in FIG. 1. In another exemplary embodiment, a plurality of additive particles 222 are disposed on the surface of the metal matrix 214 and also can be disposed in the cellular nanomatrix 216 as illustrated in FIG. 1.

Similarly, dispersed second particles 234 may be formed from coated or uncoated second powder particles 32 such as by dispersing the second powder particles 32 with the powder particles 12. In an exemplary embodiment, coated second powder particles 32 may be coated with a coating layer 36 that is the same as coating layer 16 of powder particles 12, such that coating layers 36 also contribute to the nanomatrix 216. In another exemplary embodiment, the second powder particles 232 may be uncoated such that dispersed second particles 234 are embedded within nanomatrix 216. The powder 10 and additional powder 30 may be mixed to form a homogeneous dispersion of dispersed particles 214 and dispersed second particles 234 or to form a non-homogeneous dispersion of these particles. The dispersed second particles 234 may be formed from any suitable additional powder 30 that is different from powder 10, either due to a compositional difference in the particle core 34, or coating layer 36, or both of them, and may include any of the materials disclosed herein for use as second powder 30 that are different from the powder 10 that is selected to form powder compact 200.

In a process for preparing a disintegrable implant (e.g., a pin, rod, plates, screw, nut, suture, wire, stent, staples, and the like) containing a metal composite, the process includes combining a metal matrix powder, optional disintegration agent, metal nanomatrix material, and optionally a strengthening agent to form a composition; compacting the composition to form a compacted composition; sintering the compacted composition; and pressing the sintered composition to form the component of the disintegrable implant. The members of the composition can be mixed, milled, blended, and the like to form the powder 10 as shown in FIG. 3 for example. It should be appreciated that the metal nanomatrix material is a coating material disposed on the metal matrix powder that, when compacted and sintered, forms the cellular nanomatrix. A compact can be formed by pressing (i.e., compacting) the composition at a pressure to form a green compact. The green compact can be subsequently pressed under a pressure from 15,000 psi to 100,000 psi, specifically 20,000 psi to 80,000 psi, and more specifically 30,000 psi to 70,000 psi, at a temperature from 250° C. to 600° C., and specifically 300° C. to 450° C., to form the powder compact. Pressing to form the powder compact can include compression in a mold. The powder compact can be further machined to shape the powder compact to a useful shape. Alternatively, the powder compact can be pressed into the useful shape. Machining can include cutting, sawing, ablating, milling, facing, turning, lathing, polishing, boring, bending, and the like using, for example, a mill, table saw, lathe, router, drill, brake, lapping table, electric discharge machine, and the like. Furthermore, a plurality of pieces of disintegrable implant materials can be welded together to form the disintegrable implant.

The metal composite 200 can have any desired shape or size, including that of a cylindrical billet, bar, sheet, toroid, or other form that may be machined, formed or otherwise used to form useful articles of manufacture, including various implants and implantable components. Pressing is used to form the implant or component thereof (e.g., a screw, nut, staple, and the like) from the sintering and pressing processes used to form the metal composite 200 by deforming the powder particles 12, including particle cores 14 and coating layers 16, to provide the full density and desired macroscopic shape and size of the metal composite 200 as well as its microstructure. The morphology (e.g. equiaxed or substantially elongated) of the individual particles of the metal matrix 214 and cellular nanomatrix 216 of particle layers results from sintering and deformation of the powder particles 12 as they are compacted, interdiffused, and deformed to fill the interparticle spaces of the metal matrix 214 (FIG. 1). The sintering temperatures and pressures can be selected to ensure that the density of the metal composite 200 achieves substantially full theoretical density.

The metal composite has beneficial properties for use in, for example a biological environment such as that encountered by an implant. In an embodiment, the disintegrable implant made of the metal composite has an initial shape that can be implanted or, before implantation, manipulated, e.g., by bending or elongating (such as by stretching), to be formed into an implantable shape, which can be implanted. The metal composite is strong and ductile with a percent elongation from 0.1% to 75%, specifically 0.1% to 50%, and more specifically 0.1% to 25%, based on the original size of the disintegrable implant. The metal composite has a yield strength from 15 kilopounds per square inch (ksi) to 50 ksi, and specifically 15 ksi to 45 ksi. The compressive strength of the metal composite is from 30 ksi to 100 ksi, and specifically 40 ksi to 80 ksi.

Thus, in an embodiment, the disintegrable implant has a percent elongation greater than 5%, specifically greater than 10%, more specifically greater than 15%, based on the original size of the disintegrable implant; yield strength 15 ksi to 50 ksi, and specifically 15 ksi to 45 ksi.; or compressive strength from 30 ksi to 100 ksi, and specifically 60 ksi to 80 ksi. In an embodiment, the disintegrable implant can include multiple components that are combined or interwork, e.g., a nut and screw or bolt. The components of the disintegrable implant can have the same or different material properties, such as percent elongation, compressive strength, tensile strength, and the like.

Unlike elastomeric materials, the disintegrable implant herein that includes the metal composite has a temperature rating up to 1200° F., specifically up to 1000° F., and more specifically 800° F., allowing high working temperatures for processing the implant. The disintegrable implant is temporary in that the implant is selectively and tailorably disintegrable in response to contact with a fluid or change in condition (e.g., pH, time, and the like). Moreover, in an embodiment with multiple components of the disintegrable implant, each component can have the same or different disintegration rate or reactivity with the fluid. Exemplary fluids include blood, blood substitutes (including, e.g., perfluorodecalin, porphyrins, antibiotics, vitamins, nutrients and salts), saline, organic acid, buffer (e.g., lactated Ringer's solution, sodium bicarbonate, and the like), alkaline compounds, protein, amino acids, nucleic acid, enzymes, carbohydrates (e.g., sugar (e.g., glucose), sugar alcohol, and the like), gases (e.g., $CO_2$, $O_2$, $N_2$), bone marrow, tissue, serum, plasma, urine, semen, lacrimal secretions, saliva, cerebrospinal fluid, sweat, synovial fluid, mucous secretions, lymph, antibody, antigen, or a combination thereof In an embodiment, the fluid includes halogen ions (e.g., chloride, bromide, iodide, and the like), mineral oxides (e.g., phosphate, sulfate, nitrate, and the like), organic oxides (acetate, formate, carboxylate, and the like), acids (e.g., Bronsted acid, Lewis acid, acetic acid, pyruvic acid, uric acid, hydrochloric acid, protons, hydronium, and the like), bases (Bronsted base, Lewis base, hydroxide, ammonia, urea, and the like), or a combination thereof. The properties of the fluid can depend on the identity and components of the fluid, and the chemical or physical properties of the implant can be selected depending on the fluid in order to cause disintegration of the implant over a desirable time period or tissue healing rate. Blood, as an example, contains numerous constituents such as chloride, sulfate, bromine, and trace metals. Beyond naturally occurring fluid in the human body of a patient, artificial, synthetic, or other naturally occurring fluid from another organism (e.g., another person, cadaver, or another species, e.g., flower, animal, virus, bacterium, and the like) can be used and introduced into a human to contact or disintegrate the disintegrable implant. It is contemplated that such fluid includes saline or other fluid that can include an agent that causes disintegration of the disintegrable implant herein, e.g., an agent that is a source of halogen ions or mineral oxides, and the like. In an embodiment, the fluid includes various salts such as KCl, NaCl, $ZnCl_2$, $MgCl_2$, $CaCl_2$, NaBr, $CaBr_2$, $ZnBr_2$, $NH_4Cl$, sodium formate, cesium formate, and the like. The salt can be present in the fluid in an amount from 0.2 wt. % to 50 wt. %, specifically 0.5 wt. % to 30 wt. %, and more specifically 1 wt. % to 25 wt. %, based on the weight of the composition. Moreover, the fluid can be naturally occurring or synthetic, circulating or non-circulating, or a combination thereof In yet another embodiment, the fluid is an organic acid that can include a carboxylic acid, sulfonic acid, or a combination thereof. Exemplary carboxylic acids include malic acid, tartaric acid, oxalic acid, lactic acid, propionic acid, butyric acid, ascorbic acid, citric acid, amino acids, formic acid, acetic acid, chloroacetic acid, dichloroacetic acid, trichloroacetic acid, trifluoroacetic acid, phthalic acid (including ortho-, meta- and para-isomers), and the like. Exemplary sulfonic acids include alkyl sulfonic acid or aryl sulfonic acid. Alkyl sulfonic acids include, e.g., methane sulfonic acid.

The disintegration rate (also referred to as dissolution rate) of the metal composite is 0.05 milligram per square centimeter per hour ($mg/cm^2/hr$) to 100 $mg/cm^2/hr$, specifically 0.1 $mg/cm^2/hr$ to 10 $mg/cm^2/hr$, and more specifically 0.1 $mg/cm^2/hr$ to 0.5 $mg/cm^2/hr$. The disintegration rate is variable upon the composition and processing conditions used to form the metal composite herein. Particularly, the disintegration rate is determined by the microstructure of the metal composite having the metal matrix with particle core surrounded by and in direct contact with the cellular nanomatrix. It should be appreciated that ordinary metal alloys fail to possess the control over disintegration provided by the microstructure of the metal composite herein.

Figure 4A:
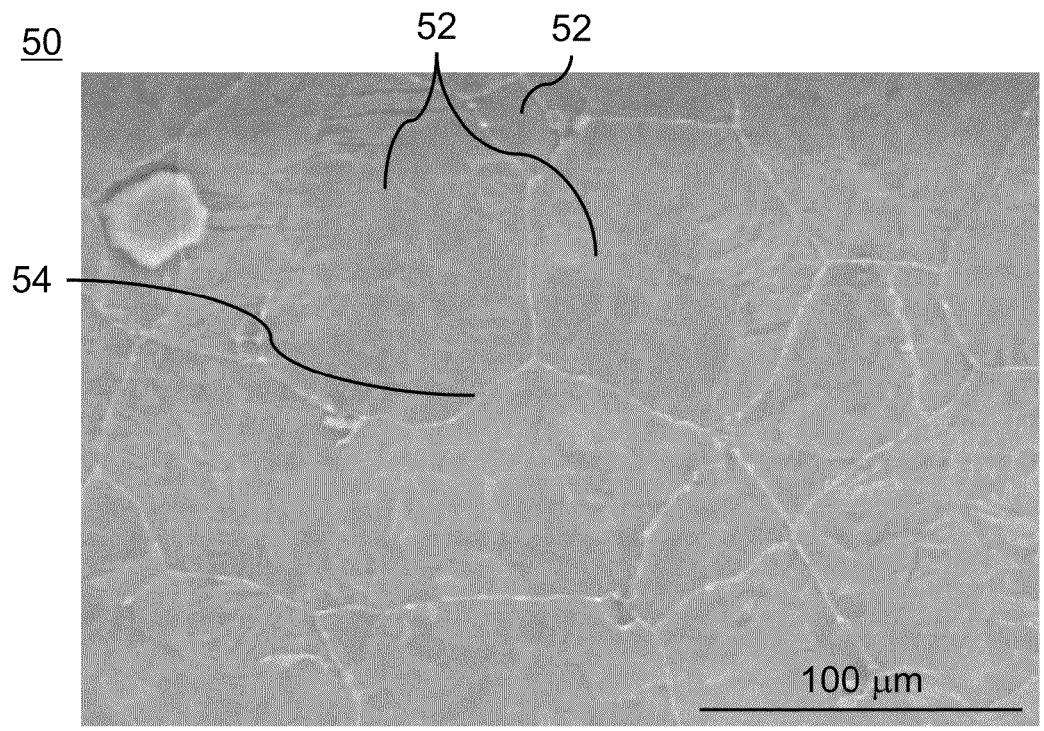
FIG. 4A is a photomicrograph of a pure metal without a cellular nanomatrix.
Figure 4B:
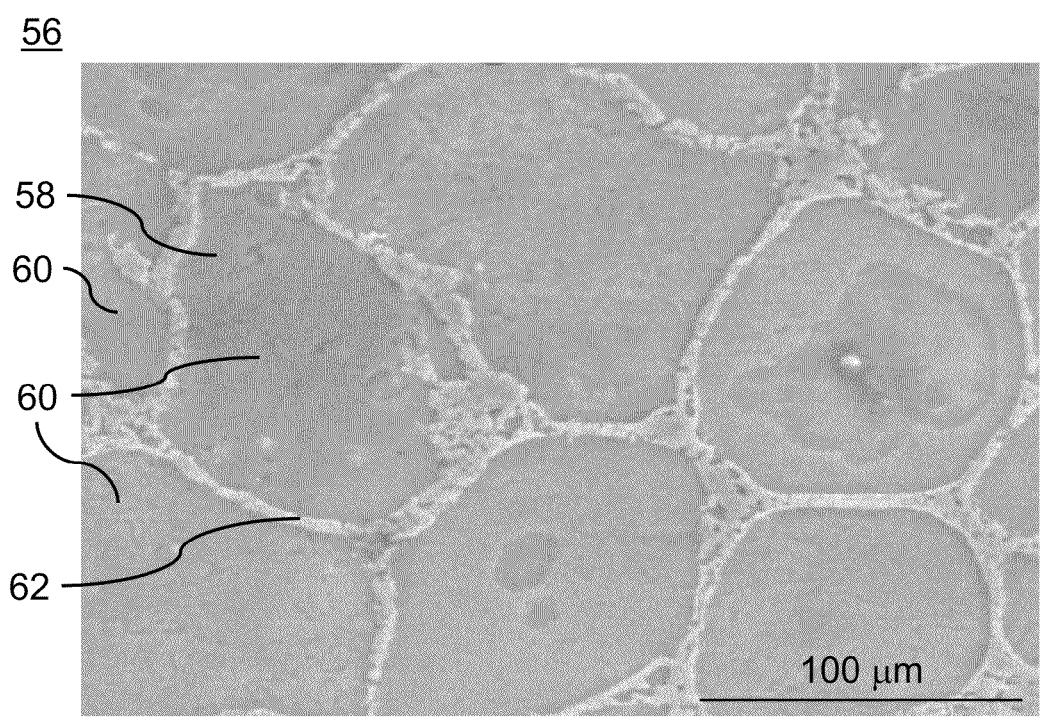
FIG. 4B is a photomicrograph of a disintegrable metal composite with a metal matrix and cellular nanomatrix.

Without wishing to be bound by theory, the unexpectedly controllable disintegration rate of the metal composite herein is due to the microstructure provided by the metal matrix and cellular nanomatrix. As discussed above, such microstructure is provided by using powder metallurgical processing (e.g., compaction and sintering) of coated powders, wherein the coating produces the nanocellular matrix, and the powder particles produce the particle core material of the metal matrix. It is believed that the intimate proximity of the cellular nanomatrix to the particle core material of the metal matrix in the metal composite produces galvanic sites for rapid and tailorable disintegration of the metal matrix. Such electrolytic sites are missing in single metals and alloys that lack a cellular nanomatrix. For illustration, FIG. 4A shows a compact 50 formed from magnesium powder. Although the compact 50 exhibits particles 52 surrounded by particle boundaries 54, the particle boundaries constitute physical boundaries between substantially identical material (particles 52), but the particle boundaries 54 and particles 52 do not have an electrochemical activity difference that controls the disintegration rate of the compact 50. Merely, the particle boundaries 54 represent points of direct contact between adjacent particles 52. However, FIG. 4B shows an exemplary embodiment of a composite metal 56 (a powder compact) that includes a metal matrix 58 having particle core material 60 disposed in a cellular nanomatrix 62. The composite metal 56 was formed from aluminum oxide coated magnesium particles where, under powder metallurgical processing, the aluminum oxide coating produces the cellular nanomatrix 62, and the magnesium produces the metal matrix 58 having particle core material 60 (of magnesium). Cellular nanomatrix 62 is not just a physical boundary as the particle boundary 54 in FIG. 4A but is also a chemical boundary interposed between neighboring particle core materials 60 of the metal matrix 58. Whereas the particles 52 and particle boundary 54 in compact 50 (FIG. 4A) do not have galvanic sites, metal matrix 58 having particle core material 60 establishes a plurality of galvanic sites in conjunction with the cellular nanomatrix 62 because the particle core material 60 of the metal matrix 58 has a different electrochemical activity than the cellular nanomatrix 62. The reactivity of the galvanic sites depend on the compounds used in the metal matrix 58 and the cellular nanomatrix 62, and the microstructure of the metal composite 56 is an outcome of the processing conditions used to form the metal matrix 58 and cellular nanomatrix 62 of the metal composite 56.

Figure 5:
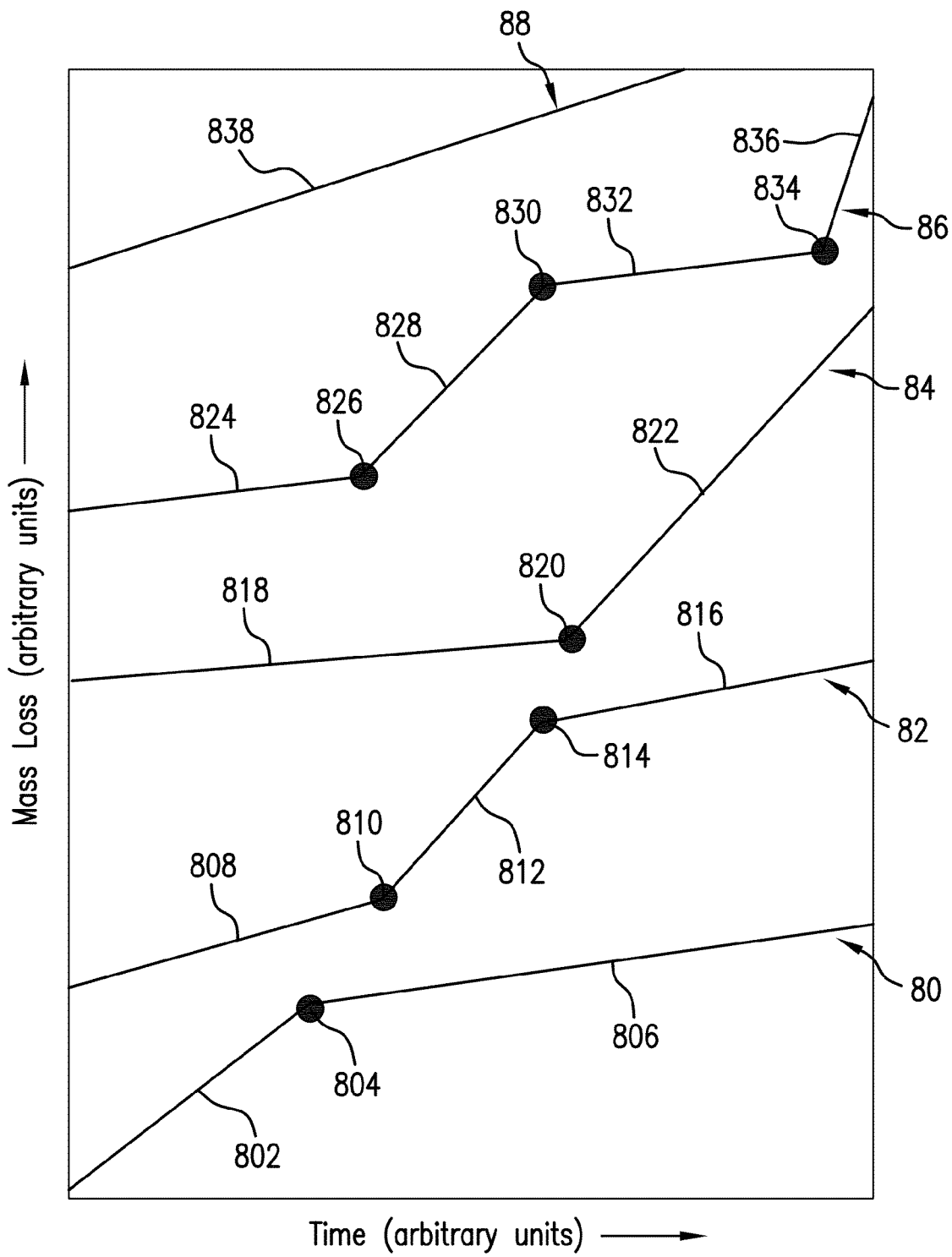
FIG. 5 is a graph of mass loss versus time for various disintegrable metal composites that include a cellular nanomatrix indicating selectively tailorable disintegration rates.

Moreover, the microstructure of the metal composites herein is controllable by selection of powder metallurgical processing conditions and chemical materials used in the powders and coatings. Therefore, the disintegration rate is selectively tailorable as illustrated for metal composites of various compositions in FIG. 5, which shows a graph of mass loss versus time for various metal composites that include a cellular nanomatrix. Specifically, FIG. 5 displays disintegration rate curves for five different metal composites (metal composite A 80, metal composite B 82 metal composite C 84, metal composite D 86, and metal composite E 88). The slope of each segment of each curve (separated by the black dots in FIG. 5) provides the disintegration rate for particular segments of the curve. Metal composite A 80 has two distinct disintegration rates (802, 806). Metal composite B 82 has three distinct disintegration rates (808, 812, 816). Metal composite C 84 has two distinct disintegration rates (818, 822), and metal composite D 86 has four distinct disintegration rates (824, 828, 832, and 836). At a time represented by points 804, 810, 814, 820, 826, 830, and 834, the rate of the disintegration of the metal composite (80, 82, 84, 86) changes due to a changed condition (e.g., presence or absence of a fluid, change of an amount of the fluid, pH, temperature, time, pressure as discussed above). The rate may increase (e.g., going from rate 818 to rate 822) or decrease (e.g., going from rate 802 to 806) along the same disintegration curve. Moreover, a disintegration rate curve can have more than two rates, more than three rates, more than four rates, etc. based on the microstructure and components of the metallic composite. Further, the disintegration rate can be constant as illustrated by the linear mass loss of metal composite E 88, having a single rate 838. In this manner, the disintegration rate curve is selectively tailorable and distinguishable from mere metal alloys and pure metals that lack the microstructure (i.e., metal matrix and cellular nanomatrix) of the metal composites described herein.

Figure 6A:
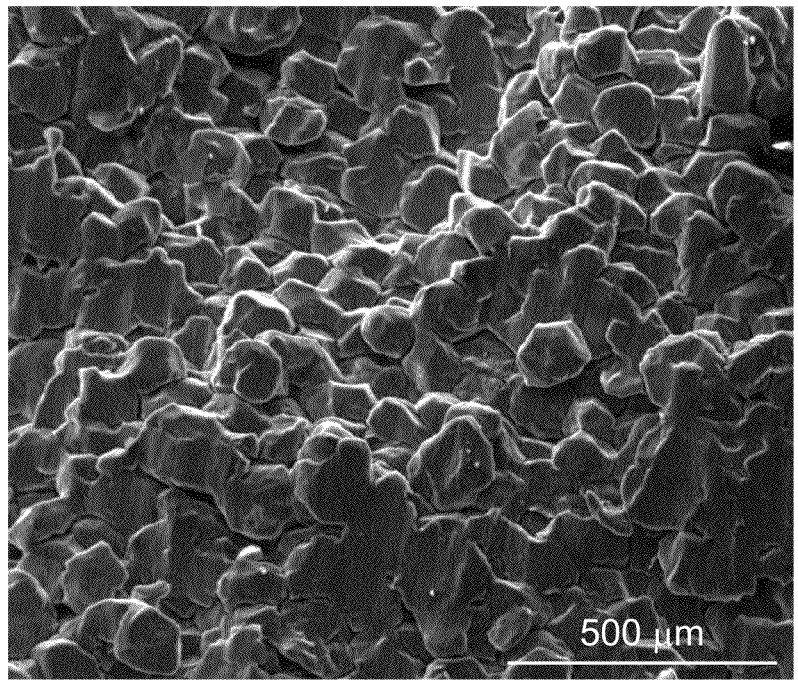
FIG. 6A is an electron photomicrograph of a fracture surface of a compact formed from a pure Mg powder.
Figure 6B:
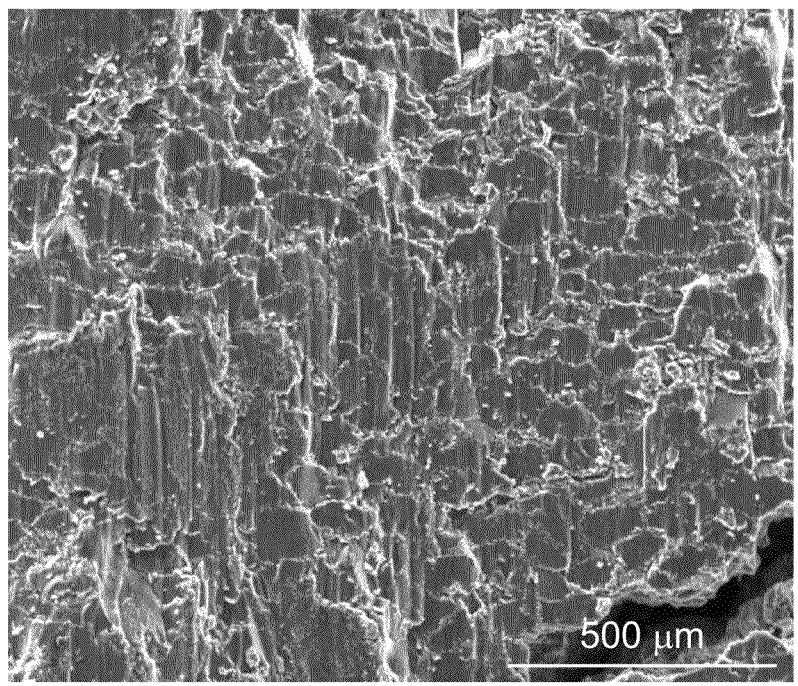
FIG. 6B is an electron photomicrograph of a fracture surface of an exemplary embodiment of a disintegrable metal composite with a cellular nanomatrix as described herein.

Not only does the microstructure of the metal composite govern the disintegration rate behavior of the metal composite but also affects the strength of the metal composite. Consequently, the metal composites herein also have a selectively tailorable material strength yield (and other material properties), in which the material strength yield varies due to the processing conditions and the materials used to produce the metal composite. To illustrate, FIG. 6A shows an electron photomicrograph of a fracture surface of a compact formed from a pure Mg powder, and FIG. 6B shows an electron photomicrograph of a fracture surface of an exemplary embodiment of a metal composite with a cellular nanomatrix as described herein. The microstructural morphology of the substantially continuous, cellular nanomatrix (FIG. 6B), which can be selected to provide a strengthening phase material, with the metal matrix (having particle core material), provides the metal composites herein with enhanced mechanical properties, including compressive strength and sheer strength, since the resulting morphology of the cellular nanomatrix/metal matrix can be manipulated to provide strengthening through the processes that are akin to traditional strengthening mechanisms, such as grain size reduction, solution hardening through the use of impurity atoms, precipitation or age hardening and strain/work hardening mechanisms. The cellular nanomatrix/metal matrix structure tends to limit dislocation movement by virtue of the numerous particle nanomatrix interfaces, as well as interfaces between discrete layers within the cellular nanomatrix material as described herein. This is exemplified in the fracture behavior of these materials, as illustrated in FIGS. 6A and 6B. In FIG. 6A, a compact made using uncoated pure Mg powder and subjected to a shear stress sufficient to induce failure demonstrated intergranular fracture. In contrast, in FIG. 6B, a metal composite made using powder particles having pure Mg powder particle cores to form metal matrix and metallic coating layers that includes Al to form the cellular nanomatrix and subjected to a shear stress sufficient to induce failure demonstrated transgranular fracture and a substantially higher fracture stress as described herein. Because these materials have high-strength characteristics, the core material and coating material may be selected to utilize low density materials or other low density materials, such as low-density metals, ceramics, glasses or carbon, that otherwise would not provide the necessary strength characteristics for use in the desired applications, including fully disintegrable medical implants and components therefore.

Figure 7:
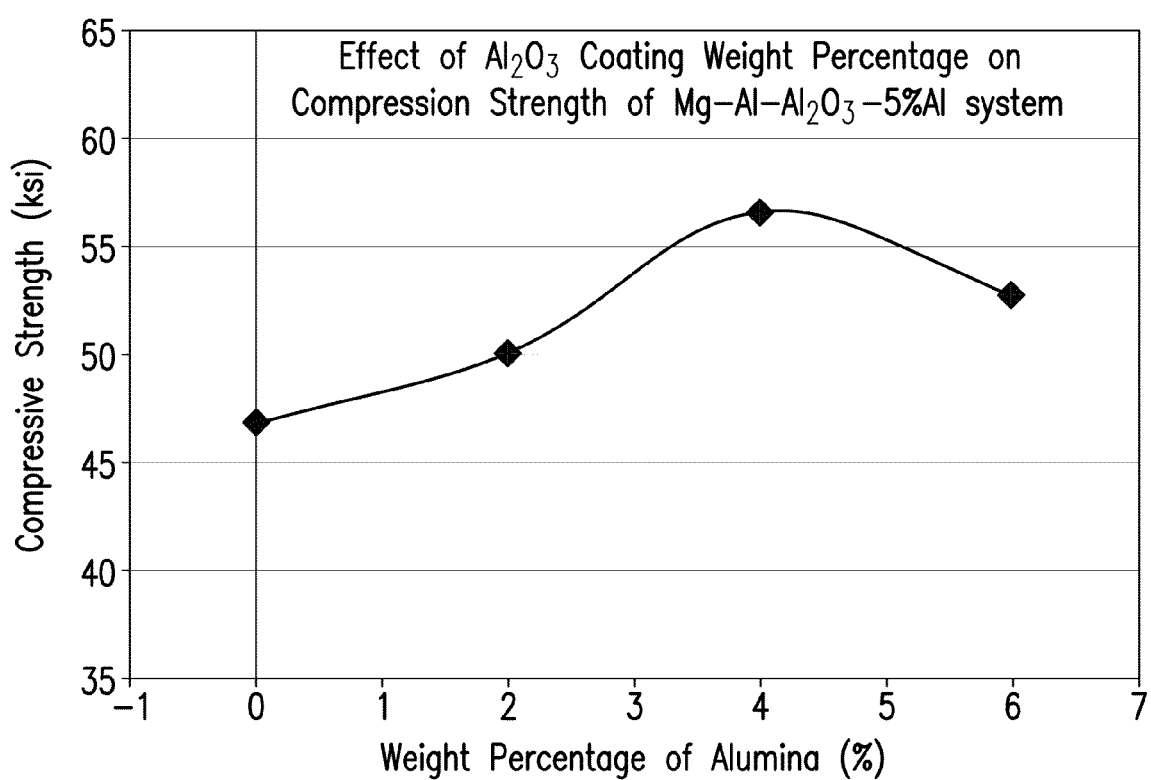
FIG. 7 is a graph of the compressive strength of a metal composite with a cellular nanomatrix versus weight percentage of a constituent (Al2O3) of the cellular nanomatrix.
Figure 8A:
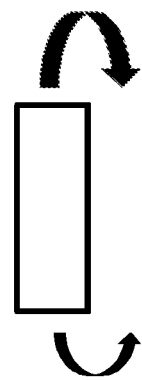
FIG. 8(A) illustrates an exemplary method to bend an implant.
Figure 8B:
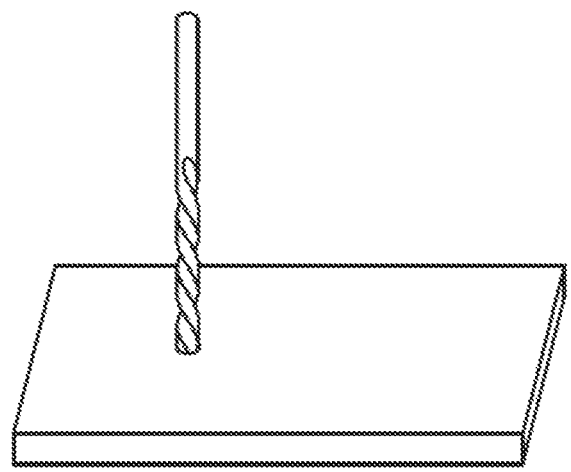
FIG. 8(B) illustrates an exemplary method to drill an implant.
Figure 8C:
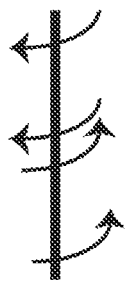
FIG. 8(C) illustrates an exemplary method to twist an implant.
Figure 8D:
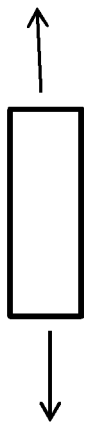
FIG. 8(D) illustrates an exemplary method to stretch an implant.
Figure 8E:
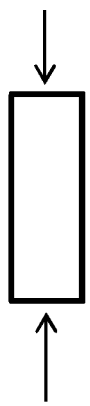
FIG. 8(E) illustrates an exemplary method to compress an implant.
Figure 9:
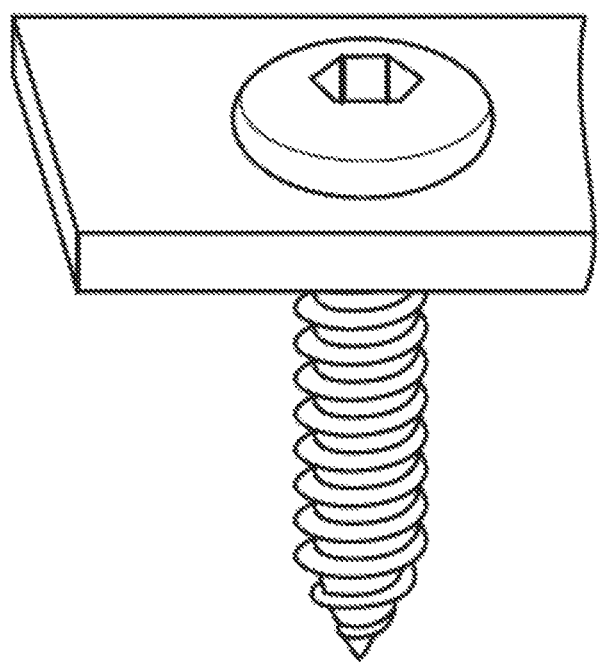
FIG. 9 illustrates an exemplary implant having multiple components.

To further illustrate the selectively tailorable material properties of the metal composites having a cellular nanomatrix, FIG. 7 shows a graph of the compressive strength of a metal composite with a cellular nanomatrix versus weight percentage of a constituent ($Al_2O_3$) of the cellular nanomatrix. FIG. 7 clearly shows the effect of varying the weight percentage (wt %), i.e., thickness, of an alumina coating on the room temperature compressive strength of a metal composite with a cellular nanomatrix formed from coated powder particles that include a multilayer ($Al/Al_2O_3/Al$) metallic coating layer on pure Mg particle cores. In this example, optimal strength is achieved at 4 wt % of alumina, which represents an increase of 21% as compared to that of 0 wt % alumina.

Thus, the metal composites herein can be configured to provide a wide range of selectable and controllable corrosion or disintegration behavior from very low corrosion rates to extremely high corrosion rates, particularly corrosion rates that are both lower and higher than those of powder compacts that do not incorporate the cellular nanomatrix, such as a compact formed from pure Mg powder through the same compaction and sintering processes in comparison to those that include pure Mg dispersed particles in the various cellular nanomatrices described herein. These metal composites 200 may also be configured to provide substantially enhanced properties as compared to compacts formed from pure metal (e.g., pure Mg) particles that do not include the nanoscale coatings described herein. Moreover, metal alloys (formed by, e.g., casting from a melt or formed by metallurgically processing a powder) without the cellular nanomatrix also do not have the selectively tailorable material and chemical properties or microstructure as the metal composites herein.

As mentioned above, the metal composite is used to produce disintegrable articles that can be used as an implant or component thereof. The material strength of the implant is several times higher than that of polymer material already in use in some implants, and the implant has a high strength to bulk ratio. As such, the implant can be used for repairing or strengthening soft or hard tissue (e.g., as an internal bone fixation). Moreover, the high ductility of the implant herein enables the implant to be manipulated (such as bending or otherwise changed) by, e.g., a surgeon, surgical technician, or machinist, so that the implant attains a particular shape or fit for implantation. In a particular embodiment, the article is a pin, rod, plate, screw, nut, suture, stent, staple, scaffold (e.g., a structure on which soft or hard tissue can grow), wire, prosthesis, nail, or a combination thereof. In another embodiment, the articles can be used alone or in combination as a disintegrable implant for repairing, strengthening, supporting, facilitating healing, or rebuilding biological tissue.

Moreover, the implant herein has a high level of strength, shock absorption, and resistance to stress and strain and maintains compliance and flexibility in order to accommodate various implant sites, areas, or anatomical structures. Because the implant disintegrates over time, tissue in which the implant is disposed has access to adequate mass transfer (e.g., between plasma and tissue) so that the tissue can repair or grow without adverse limitation from the disintegrable implant.

According to an embodiment, a disintegrable implant includes the metal composite having the cellular nanomatrix comprising the metallic nanomatrix material and the metal matrix disposed in the cellular nanomatrix such that the implant is configured to disintegrate in response to contact with the fluid. In an embodiment, the implant includes a plurality of components, and each component is made of a metal composite and has a same or different disintegration rate. In one embodiment, the plurality of components includes a first component and a second component attached to or interworking with the first component. In a particular embodiment, the implant is a disintegrable dynamic hip screw implant having a slide plate and lag screw dynamically disposable in a through-bore of the slide plate. The implant further comprises a plurality of screws to attach the slide plate to a tissue (e.g., a femur). The lag screw can telescopically translate in the bore for fixation while allowing impaction to occur at, e.g., a fracture in a hip during healing and weight bearing. It is contemplated that each component (slide plate, lag screw, and plurality of screws) of the implant are made of the metal composite and removable non-surgically from a patient such as by disintegration in response to contact with a fluid.

It should be appreciated that the disintegration rates of the components of the implant are independently selectively tailorable as discussed above, and that the components of the implant can have independently selectively tailorable material properties such as yield strength, compressive strength, and disintegration rate.

The disintegrable implant herein can have beneficial properties for use in, for example a biological environment. The implant can be completely disintegrable and can be part of a completely disintegrable implant system. Further, the implant has mechanical and chemical properties of the metal composite described herein. The implant thus beneficially is selectively and tailorably disintegrable in response to contact with a fluid or change in condition (e.g., presence, absence, or change in amount of the fluid, pH, time, and the like). Exemplary fluids include blood, saline, tissue, organic acid, or a combination thereof.

Although some metallic alloys, particularly magnesium alloy, can have negative side effects that include subcutaneous gas bubbles or alkalization of body fluid due to fast and uncontrolled disintegration of the implant material, the implant herein has a microstructure of the metal composite (i.e., the metal matrix disposed in the cellular nanomatrix) that avoids production of a large amount of gas or hydroxide. As an example, magnesium can react with water to produce hydrogen and hydroxide. In a large enough quantity, the hydrogen can from bubbles in vitro, which could impair tissue repair. In addition, hydroxide produced too rapidly could increase the pH of the tissue and environment surrounding an implant. The implant herein overcomes these limitations by selection of the relative amount of the metal matrix and nanomatrix, size of metal matrix particle core relative to the size (e.g., cross-sectional area) of the cellular nanomatrix, and relative homogeneity of the microstructure of the metal composite.

The disintegrable implant can have any shape. Exemplary shapes include a rod, pin, screw, plane, cone, ellipsoid, toroid, sphere, cylinder, their truncated shapes, asymmetrical shapes, including a combination of the foregoing, and the like.

In addition to being selectively corrodible, the implant herein can deform in situ, e.g., to conform to a space in which it is disposed or other shape. The shape can be due to pressure exerted onto the implant before implantation or after implantation. Further, the pressure can occur in vivo by a patient's anatomical structure or in vitro by, e.g., machining or other bending process. According to an embodiment, the implant maintains the implanted shape, i.e., the shape of the implant prior to implantation in the patient. Deformation of the implant can occur in any direction, e.g., a radial direction, a length direction, and the like. The deformation can include stretching, compressing, twisting, and the like. Thus, the implant can be a temporary implant with an initial shape that can be implanted and subsequently deformed under pressure or can be deformed prior to implantation, e.g., by a surgeon or surgical technician. To achieve the resiliency and deformation properties, the implant has a percent elongation from 1% to 25%, specifically 1% to 20%, based on the original size of the implant. The implant has a yield strength from 15 ksi to 50 ksi, and specifically 15 ksi to 45 ksi. The compressive strength of the implant is from 30 ksi to 100 ksi, and specifically 40 ksi to 80 ksi.

Unlike other implantable materials such as a polymer, the implant herein that includes the metal composite has a temperature rating up to 1200° F., specifically up to 1000° F., and more specifically up to 800° F. The elevated temperature allows high temperature working or processing of the implant and also sterilizing of the implant pre-, intra-, inter-, or post-operatively, e.g., by autoclaving, infrared heating, and the like. The implant is temporary in that the implant is selectively and tailorably disintegrable in response to contact with a fluid.

Since the implant can interwork with other anatomical components, e.g., a soft or hard tissue, the properties of the implant are selected for the appropriate selectively tailorable material and chemical properties. These properties are a characteristic of the metal composite and the processing conditions that form the metal composite, which is used to produce the implant. In an embodiment, the metal composite has a plurality of components, and the components of the implant can differ from one another compositionally. In this way, the components of the implant can have independent selectively tailorable mechanical and chemical properties.

In an embodiment, a component of the implant has a different amount of a strengthening agent than another component, for example, where a higher strength component has a greater amount of a certain metal or strengthening agent than does a component of lesser strength. Thus, under a compressive, tensile, or shear force, a first component of the implant can deform before deformation of a second component.

A factor that impacts the selectively tailorable material and chemical properties of the implant is the constituents of the metal composite, i.e., the metallic nanomatrix of the cellular nanomatrix, the metal matrix disposed in the cellular nanomatrix, or the disintegration agent. The compressive and tensile strengths and disintegration rate are determined by the chemical identity and relative amount of these constituents. Thus, these properties can be regulated by the constituents of the metal composite. According to an embodiment, the implant has a metal matrix of the metal composite that includes a pure metal. In an embodiment, the implant has a metal matrix that includes an alloy. It is contemplated that the implant can be functionally graded in that the metal matrix of the metal composite such that it can contain a pure metal or an alloy having a gradient in the relative amount of either the pure metal or alloy in the metal matrix as disposed in the implant. Therefore, the value of the selectively tailorable properties varies in relation to the position along the implant.

The disintegrable implant herein can be augmented with various materials. In one embodiment, the implant can include a bioabsorbable or biodegradable material, e.g., a polymer such as polyglycolic acid, polylactic acid, polydioxanone, caprolactone, polycaprolactone (PCL), polycaprolactone-polylactide copolymer (e.g., polycaprolactone-polylactide random copolymer), polycaprolactone-polyglycolide copolymer (e.g., polycaprolactone-polyglycolide random copolymer), polycaprolactone-polylactide-polyglycolide copolymer (e.g., polycaprolactone-polylactide-polyglycolide random copolymer), polylactide, polycaprolactone-poly(β-hydroxybutyric acid) copolymer (e.g., polycaprolactone-poly(β-hydroxybutyric acid) random copolymer) poly(β-hydroxybutyric acid), polyvinyl alcohol, polyethylene glycol, polyanhydrides, polyiminocarbonates, and the like. According to an embodiment, the implant can include a bioabsorbable or biodegradable ceramic such as beta-tertiary calcium phosphate (β-TCP), hydroxy apatite, or combination thereof In some embodiments, the implant can include a non-bioabsorbable or non-biodegradable material, e.g., a non-metal composite pure metal or alloy, polymer (e.g., polytetrafluoroethylene, acrylic resin, silicone, and the like), ceramic, and the like. However, unless explicitly stated (e.g., in an explicit recitation in a claim appended hereto or within an embodiment), the implant does not include non-bioabsorbable or non-biodegradable material.

As described herein, the implant can be used in a biological environment, e.g., for repairing, strengthening, supporting, or facilitating healing of biological tissue. In an embodiment, a method for repairing tissue includes disposing an implant in a patient. The implant includes a metal composite that includes a cellular nanomatrix comprising a metallic nanomatrix material and a metal matrix disposed in the cellular nanomatrix. The method also includes contacting tissue of the patient with the implant, wherein the tissue is in need of repair, and non-operatively removing the implant to repair the tissue.

The implant can be attached to one or more tissues, and the tissues can be the same or different. The implant can be self-attaching (i.e., not requiring any additional material in order to attach to a tissue), can attach to tissue with a supplemental fastener (e.g., a suture), or a combination thereof. Here, an incision can be made in the patient's skin and the implant disposed in the patient and attached to tissue therein. Attachment can be made via a portion of the implant or a component of the implant (e.g., a screw inserted through a plate, wherein the screw is driven into bone). Such attachment depends on the tissue to be repaired and the type of repair warranted, which can be determined by one skilled in the art.

After implantation, the incision can be closed, e.g., by suturing, stapling, etc. The implant is left in place, provides stability to the tissue during healing, and accommodates growing tissue and replacement of the implant due to disintegration of the implant. Moreover, the implant can disintegrate completely but will remain until full regeneration of the tissue, e.g., bone structure, which can require weeks to more than a year. The disintegrable implant thus can have a disintegration rate selected based upon the tissue to be repaired and also to disintegrate and be removed in equilibrium with the tissue healing process. The implant is versatile in application such that the tissue can include soft tissue (e.g., cartilage, muscle, skin, and the like), hard tissue (e.g., bone, tooth, and the like), or a combination thereof.

It is contemplated that the implant can include a plurality of components. In an embodiment, the implant includes a first implant component and a second implant component that connects to or interworks with the first implant component.

The implant has a lifetime governed by its microstructure and also its surface area, composition, and the type of fluid it contacts as well as environmental parameters such as the temperature. In an embodiment, the implant has an in vitro lifetime from 5 hours to 5 years, specifically 1 day to 2 years, more specifically 3 days to 15 months, even more specifically 5 days to 12 months, and yet more specifically 2 weeks to 8 months, based on the presence of the implant in tissue while still providing support to the tissue. According to an embodiment, the implant has an in vitro lifetime effective for the implant to stabilize the tissue during repair and to disintegrate at a rate such that an amount of gas production and blood alkalization from a product of disintegrating the implant is biologically tolerable and non-toxic to the patient.

Non-operatively removing the implant comprises disintegrating the implant by contacting the implant with a fluid that can include blood, a blood substitute, saline, a salt, an organic acid, a buffer, an alkaline compound, a protein, an amino acid, a nucleic acid, an enzyme, a carbohydrate, a gas, bone marrow, a tissue, serum, plasma, urine, semen, a lacrimal secretion, saliva, cerebrospinal fluid, sweat, synovial fluid, a mucous secretion, lymph, or a combination thereof. Thus, unlike corrosion-resistant implants, the disintegrable implant disintegrates in vivo in contact with the fluid so that the implant does not need to be removed by a subsequent operation.

Consequently, the implant herein is useful for repairing, strengthening, supporting, facilitating healing biological tissue. Moreover, the disintegrable implant is robust. According to an embodiment, repairing tissue can further include sterilizing the implant by a chemical or physical process, which includes contacting the implant with a chemical, irradiating the implant, or mechanically removing non-metal composite material from the implant. The chemical or physical process removes or causes removal of contaminants (e.g., bacteria, virus, molds, spores, biological material, particles, molecules, atoms, and the like) from the implant (either the surface or bulk) or for such contaminants to become dormant and biologically inert or unharmful to a patient. The chemical can be an alcohol (e.g., ethanol, a propanol, and the like), halogenated compound (e.g., chlorine, bromine, iodine), medicament (e.g., antiseptic, antibacterial, bacteriostat), disinfectant, pharmaceutical, and the like. The physical process can include scrubbing, sanding, and the like or irradiating the implant with ultraviolet, X-ray, visible, or infrared radiation.

Moreover, the implant can be manipulated before implantation. Manipulation of the implant includes bending, drilling, twisting, compressing, stretching the implant prior to disposing the implant in the patient, or a combination thereof. In case the surgeon finds that the implant is not the size or shape, the implant can be removed and manipulated to the correct size or shape, sterilized if wanted, and implanted again into the patient.

The metal composite, articles, and methods are further illustrated by the following non-limiting example.

A disintegrable implant screw was prepared by loading magnesium particles (average particle size of 100 μm) into a chemical vapor deposition (CVD) reactor and coating the magnesium particles aluminum by chemical vapor deposition at 350 to 400° C. for 30 to 45 minutes. The resulting powder of aluminum coated magnesium particles (5 wt % Al coating, 95 wt % Mg core) was transferred from the CVD reactor to a press and subjected to cold isostatic pressing at room temperature at a pressure of 30,000 pounds per square inch (psi) for 15 to 30 minutes to form a green compact. The green compact was subsequently extruded into a cylindrical rod of diameter 8 millimeters (mm) and length of 10 meters (m), which was machined into screws of 6 mm diameter by 15 mm length, having a metal composite of a matrix of magnesium particles in a nanomatrix of aluminum. The screw had a theoretical density of 1.78 grams per milliliter (g/mL) and empirical weight of 5 g.

The screw was immersed into a disintegration vessel filled with an aqueous solution of 3 wt % KCl, based on the weight of the solution, held at 80° F. (26° C.). As the screw disintegrated, its mass loss was determined periodically over 48 hours by weighing the dry screw, which was subsequently returned to the disintegration vessel. After 48 hours, the final weight of the screw was 4.9868 g. The average rate of disintegration (corrosion) of the screw was 0.5 mg/cm$^2$/hour or 1.35 mg/hour, and the total time to dissolve the screw was 3703 hours, or 154 days.

Mechanical testing of screws obtained from the powder and processed identically as above was performed. The screws had an average ultimate tensile strength of 35 ksi, elongation of 6%, and ultimate compressive strength of 60 ksi, elongation at compressive failure of 12%.

While one or more embodiments have been shown and described, modifications and substitutions may be made thereto without departing from the spirit and scope of the invention. Accordingly, it is to be understood that the present invention has been described by way of illustrations and not limitation. Embodiments herein can be used independently or can be combined.

All ranges disclosed herein are inclusive of the endpoints, and the endpoints are independently combinable with each other. The ranges are continuous and thus contain every value and subset thereof in the range. Unless otherwise stated or contextually inapplicable, all percentages, when expressing a quantity, are weight percentages. The suffix "(s)" as used herein is intended to include both the singular and the plural of the term that it modifies, thereby including at least one of that term (e.g., the colorant(s) includes at least one colorants). "Optional" or "optionally" means that the subsequently described event or circumstance can or cannot occur, and that the description includes instances where the event occurs and instances where it does not. As used herein, "combination" is inclusive of blends, mixtures, alloys, reaction products, and the like.

As used herein, "a combination thereof" refers to a combination comprising at least one of the named constituents, components, compounds, or elements.

All references are incorporated herein by reference.

The use of the terms "a" and "an" and "the" and similar referents in the context of describing the invention (especially in the context of the following claims) are to be construed to cover both the singular and the plural, unless otherwise indicated herein or clearly contradicted by context. "Or" means "and/or." It should further be noted that the terms "first," "second," and the like herein do not denote any order, quantity, or importance, but rather are used to distinguish one element from another. The modifier "about" used in connection with a quantity is inclusive of the stated value and has the meaning dictated by the context (e.g., it includes the degree of error associated with measurement of the particular quantity). The conjunction "or" is used to link objects of a list or alternatives and is not disjunctive; rather the elements can be used separately or can be combined together under appropriate circumstances.

What is claimed is:

1. A method for repairing tissue, the method comprising:
disposing an implant in a patient, the implant comprising a metal composite which comprises:
a cellular nanomatrix comprising a metallic nanomatrix material; and
a metal matrix disposed in the cellular nanomatrix;
contacting tissue of the patient with the implant, the tissue being in need of repair; and
allowing the implant to disintegrate as the tissue repairs;
wherein the metal matrix comprises a particle core material that is discontinuously and discretely distributed as particles within the metal composite.

2. The method of claim 1, wherein allowing the implant to disintegrate comprises disintegrating the implant by contacting the implant with a fluid comprising blood, a blood substitute, saline, a salt, an organic acid, a buffer, an alkaline compound, a protein, an amino acid, a nucleic acid, an enzyme, a carbohydrate, a gas, bone marrow, a tissue, serum, plasma, urine, semen, a lacrimal secretion, saliva, cerebrospinal fluid, sweat, synovial fluid, a mucous secretion, lymph, or a combination thereof.

3. The method of claim 2, wherein the disposing step comprises disposing an implant that has an in vitro lifetime effective for the implant to stabilize the tissue during repair and to disintegrate at a rate such that an amount of gas production and blood alkalization from a product of disintegrating the implant is biologically tolerable and non-toxic to the patient.

4. The method of claim 1, further comprising bending, drilling, twisting, compressing, stretching the implant, or a combination thereof, prior to disposing the implant in the patient.

5. The method of claim 1, further comprising growing additional tissue on the implant.

6. The method of claim 1, wherein the disposing step comprises disposing an implant that has a nanoscale thickness between adjacent particles of the metal matrix.

7. The method of claim 1, wherein the disposing step comprises disposing an implant that has the metal matrix comprising magnesium; and the metallic nanomatrix material comprising aluminum, calcium, cobalt, copper, iron, molybdenum, nickel, silicon, zinc, an intermetallic compound thereof, or a combination thereof.

8. The method of claim 7, wherein the disposing step comprises disposing an implant that has the metal matrix further comprising aluminum, calcium, copper, iron, manganese, zinc, or a combination thereof.

9. The method of claim 7, wherein the disposing step comprises disposing an implant that has the metal matrix in the form of an alloy.

10. The method of claim 1, wherein the disposing step comprises disposing an implant that has the metal matrix comprising magnesium and the metallic nanomatrix material comprising aluminum oxide.

11. The method of claim 1, wherein the disposing step comprises disposing an implant that has the metal composite further comprising a disintegrating agent comprising cobalt, copper, iron, nickel, or a combination comprising at least one of the foregoing.

12. The method of claim 1, wherein the disposing step comprises disposing an implant that has a disintegration rate from 0.1 $mg/cm^2/hr$ to 100 $mg/cm^2/hr$.

13. The method of claim 1, wherein the disposing step comprises disposing an implant that has a percent elongation from 0.1% to 25% and a compressive strength of about 30 ksi to about 80 ksi.

14. The method of claim 1, wherein the disposing step comprises disposing an implant comprising a plurality of components, each component comprising the metal composite and having a same or different disintegration rate.

15. The method of claim 14, wherein the disposing step comprises disposing an implant wherein the plurality of components comprises:
    a first component; and
    a second component attached to or interworking with the first component.

\* \* \* \* \*